(12) United States Patent
Siciliano (10) Patent No.: US 12,415,060 B2
(45) Date of Patent: Sep. 16, 2025

(54) ELECTROMAGNETICALLY DRIVEN TATTOO MACHINE AND SYSTEM

(71) Applicant: FK Irons Inc., Doral, FL (US)

(72) Inventor: Gaston Siciliano, Miami, FL (US)

(73) Assignee: FK Irons Inc., Doral, FL (US)

( * ) Notice: Subject to any disclaimer, the term of this patent is extended or adjusted under 35 U.S.C. 154(b) by 0 days.

(21) Appl. No.: 17/878,387

(22) Filed: Aug. 1, 2022

(65) Prior Publication Data

US 2022/0362535 A1 Nov. 17, 2022

Related U.S. Application Data (63) Continuation of application No. 16/158,290, filed on Oct. 11, 2018, now Pat. No. 11,400,268.

(51) Int. Cl.
*A61M 37/00* (2006.01)

(52) U.S. Cl.
CPC . *A61M 37/0076* (2013.01); *A61M 2205/0288* (2013.01); *A61M 2205/3317* (2013.01); *A61M 2205/3606* (2013.01); *A61M 2205/8206* (2013.01)

(58) Field of Classification Search
CPC .............. A61M 37/00; A61M 37/0015; A61M 37/0076; A61M 2037/0046; A61M 2037/0061; A61M 37/0084; A61M 2205/0288; A61M 2205/3317; A61M 2205/3606; A61M 2205/8206; A01K 11/005; A45D 34/04; B26F 1/28
See application file for complete search history.

(56) References Cited

U.S. PATENT DOCUMENTS

| | | | |
|---|---|---|---|
| 2,588,623 | A | 3/1952 | Eliscu |
| D226,829 | S | 5/1973 | Staub |
| D229,869 | S | 1/1974 | Staub |
| D241,475 | S | 9/1976 | Staub |
| 4,137,632 | A | 2/1979 | Pfanzer |
| 4,159,659 | A | 7/1979 | Nightingale |
| D254,150 | S | 2/1980 | Barton |
| D288,359 | S | 2/1987 | Hoff |
| 4,644,952 | A | 2/1987 | Patipa |
| 4,647,260 | A | 3/1987 | O'Hara |

(Continued)

FOREIGN PATENT DOCUMENTS

| | | |
|---|---|---|
| CA | 2412681 | 5/2003 |
| CA | 2785667 | 2/2013 |

(Continued)

*Primary Examiner* — Robert J Scruggs
(74) *Attorney, Agent, or Firm* — Akerman LLP; Peter A. Chiabotti (57) ABSTRACT

A magnetically driven tattoo machine is disclosed, which has a substantially radially symmetric exterior shape and be driven by a sensor-controlled electromagnetic coil. The machine has no oscillating mechanical components, and thus reduces or eliminates vibration. The machine may include a housing mechanically isolated from a needle cartridge or subcomponents that can be disassembled and sterilized. The electromagnet may be controlled by a sensor integral with the coil, housed within the machine, or within an external power supply. The machine may be powered by internal battery or by an external power source. The machine may also be controlled wirelessly.

19 Claims, 3 Drawing Sheets

(56) References Cited

U.S. PATENT DOCUMENTS

| | | | |
|---|---|---|---|
| 4,665,912 A | 5/1987 | Burton | |
| 4,719,825 A | 1/1988 | LaHaye | |
| D294,388 S | 2/1988 | Hardy | |
| D294,519 S | 3/1988 | Hardy | |
| 4,796,624 A | 1/1989 | Trott | |
| 5,032,043 A | 7/1991 | Hollifield | |
| 5,279,552 A | 1/1994 | Magnet | |
| 5,341,704 A | 8/1994 | Klemm | |
| 5,380,132 A | 1/1995 | Parks | |
| 5,471,102 A * | 11/1995 | Becker | B26F 1/24 |
| | | | 604/289 |
| D364,923 S | 12/1995 | Chou | |
| 5,586,473 A | 12/1996 | Chou | |
| 5,601,387 A | 2/1997 | Sanford | |
| D380,046 S | 6/1997 | Domanowski | |
| D389,578 S | 1/1998 | Emerson | |
| D389,915 S | 1/1998 | Emerson | |
| 5,776,158 A | 7/1998 | Chou | |
| 6,033,421 A | 3/2000 | Theiss | |
| 6,040,752 A * | 3/2000 | Fisher | H01F 7/1615 |
| | | | 335/229 |
| D433,752 S | 11/2000 | Saravia | |
| D434,149 S | 11/2000 | Mirhashemi | |
| D439,337 S | 3/2001 | Jones | |
| D440,310 S | 4/2001 | Laks | |
| 6,263,762 B1 | 7/2001 | Zeitler | |
| D448,483 S | 9/2001 | Behnke | |
| D453,833 S | 2/2002 | Hess | |
| D457,955 S | 5/2002 | Bilitz | |
| D465,279 S | 11/2002 | Etter | |
| 6,505,530 B2 | 1/2003 | Adler | |
| 6,550,356 B1 | 4/2003 | Underwood | |
| 6,596,007 B2 | 7/2003 | Evans | |
| 6,639,496 B1 | 10/2003 | van Namen | |
| D490,152 S | 5/2004 | Myall | |
| D493,530 S | 7/2004 | Reschke | |
| D493,532 S | 7/2004 | Levaughn | |
| 6,772,656 B2 | 8/2004 | Godoy | |
| 6,950,004 B2 | 9/2005 | Gaday | |
| D521,641 S | 5/2006 | Reschke | |
| D535,396 S | 1/2007 | Reschke | |
| D536,451 S | 2/2007 | Haydu | |
| D538,934 S | 3/2007 | Wilkinson | |
| D538,936 S | 3/2007 | Bohmel | |
| 7,211,097 B2 | 5/2007 | Carrasco | |
| 7,225,708 B2 | 6/2007 | Chen | |
| D549,325 S | 8/2007 | Schnitzler | |
| D549,779 S | 8/2007 | Shimizu | |
| D560,803 S | 1/2008 | Tasse | |
| 7,335,211 B2 | 2/2008 | Chen | |
| 7,337,697 B2 | 3/2008 | Bader | |
| D575,343 S | 8/2008 | Cetera | |
| 7,442,042 B1 | 10/2008 | Lewis | |
| D581,530 S | 11/2008 | Thierfelder | |
| D582,981 S | 12/2008 | Bhavnani | |
| D586,465 S | 2/2009 | Faulkner | |
| 7,518,479 B2 * | 4/2009 | Mask | A61M 37/0084 |
| | | | 335/212 |
| D597,668 S | 8/2009 | Woodruff | |
| D612,051 S | 3/2010 | Ruf | |
| D621,042 S | 8/2010 | Ruf | |
| D622,000 S | 8/2010 | Kluge | |
| 7,810,414 B2 | 10/2010 | Hsu | |
| D628,293 S | 11/2010 | Ruf | |
| D628,695 S | 12/2010 | Ruf | |
| D634,426 S | 3/2011 | Zollers | |
| 7,908,943 B2 | 3/2011 | Beyer | |
| D638,939 S | 5/2011 | Eikhoff | |
| D645,965 S | 9/2011 | Muto | |
| 8,171,825 B1 | 5/2012 | Adams | |
| D664,657 S | 7/2012 | Vieira | |
| D667,554 S | 9/2012 | Casabonne | |
| 8,328,738 B2 | 12/2012 | Frankhouser et al. | |
| 8,356,533 B2 | 1/2013 | Forth | |
| D677,790 S | 3/2013 | Little | |
| 8,393,249 B2 | 3/2013 | Gaday | |
| D679,396 S | 4/2013 | Jan | |
| 8,414,531 B2 | 4/2013 | Oginski et al. | |
| D691,263 S | 10/2013 | Chen | |
| 8,771,308 B2 | 7/2014 | Lin | |
| 8,794,109 B2 | 8/2014 | Lee | |
| 8,870,865 B2 | 10/2014 | Frankhouser | |
| 8,920,379 B2 | 12/2014 | Lee | |
| D723,685 S | 3/2015 | Myers | |
| 9,050,445 B2 | 6/2015 | Klebs | |
| D736,915 S | 8/2015 | Schultz | |
| D737,441 S | 8/2015 | Presser | |
| D737,972 S | 9/2015 | Chen | |
| 9,126,027 B2 | 9/2015 | Lin | |
| D743,546 S | 11/2015 | Jayaraj | |
| D745,152 S | 12/2015 | Mayer | |
| D750,243 S | 2/2016 | Tetzlaff | |
| D750,258 S | 2/2016 | Crossley | |
| 9,259,561 B2 | 2/2016 | Lee | |
| D762,303 S | 7/2016 | Jayaraj | |
| 9,393,395 B2 | 7/2016 | Miller | |
| D763,443 S | 8/2016 | Chen | |
| D765,841 S | 9/2016 | Schuerg | |
| D765,842 S | 9/2016 | Schuerg | |
| D766,432 S | 9/2016 | Schuerg | |
| 9,504,814 B2 | 11/2016 | Frister | |
| D779,670 S | 2/2017 | Krystyniak | |
| D781,419 S | 3/2017 | Bojanowski | |
| D782,041 S | 3/2017 | Pell | |
| D782,667 S | 3/2017 | Fuhr | |
| D785,795 S | 5/2017 | Amano | |
| 9,662,483 B2 | 5/2017 | Siciliano | |
| D791,946 S | 7/2017 | Schwartz | |
| D791,947 S | 7/2017 | Chen | |
| 9,707,385 B1 | 7/2017 | Chen | |
| D794,192 S | 8/2017 | Schuerg | |
| D794,193 S | 8/2017 | Schuerg | |
| D794,194 S | 8/2017 | Schuerg | |
| 9,788,763 B1 * | 10/2017 | Demas | A61B 5/681 |
| D803,398 S | 11/2017 | Israni | |
| D805,195 S | 12/2017 | Lee | |
| D805,196 S | 12/2017 | Lee | |
| D805,197 S | 12/2017 | Lee | |
| D805,198 S | 12/2017 | Lee | |
| D805,640 S | 12/2017 | Lee | |
| D815,738 S | 4/2018 | Ye | |
| D819,207 S | 5/2018 | Blank | |
| 9,987,468 B2 | 6/2018 | Bagwell | |
| D831,208 S | 10/2018 | Benisty | |
| D837,371 S | 1/2019 | Zu | |
| D837,372 S | 1/2019 | Zu | |
| D839,425 S | 1/2019 | Zanata | |
| 10,449,346 B2 | 10/2019 | Juan | |
| 10,549,110 B1 * | 2/2020 | Schwarz | A61N 2/02 |
| 2003/0171767 A1 * | 9/2003 | Koplen | A61M 37/0076 |
| | | | 606/185 |
| 2003/0195542 A1 | 10/2003 | Lee | |
| 2004/0116953 A1 * | 6/2004 | Dixon | A61M 37/0076 |
| | | | 606/186 |
| 2005/0055042 A1 | 3/2005 | Carrasco | |
| 2006/0020283 A1 | 1/2006 | Lisec | |
| 2008/0055028 A1 | 3/2008 | Mask et al. | |
| 2008/0287978 A1 | 11/2008 | Hickman | |
| 2008/0306502 A1 | 12/2008 | Lisec | |
| 2010/0036317 A1 | 2/2010 | Dginski | |
| 2011/0048174 A1 | 3/2011 | Lin | |
| 2012/0041374 A1 | 2/2012 | Lee | |
| 2012/0123462 A1 | 5/2012 | Lee | |
| 2012/0179134 A1 | 7/2012 | Garitano | |
| 2012/0279330 A1 | 11/2012 | Lin | |
| 2013/0123825 A1 | 5/2013 | Demjanenko | |
| 2013/0138130 A1 | 5/2013 | Nizov | |
| 2014/0018835 A1 | 1/2014 | Scherkowski | |
| 2014/0094837 A1 | 4/2014 | Danenberg | |
| 2014/0358172 A1 | 12/2014 | Lin | |
| 2014/0358173 A1 | 12/2014 | Lin | |
| 2015/0025561 A1 | 1/2015 | La Fontaine | |
| 2015/0202420 A1 | 7/2015 | Miller | |
| 2015/0352346 A1 | 12/2015 | Webb | |

(56) References Cited

U.S. PATENT DOCUMENTS

| | | |
|---|---|---|
| 2015/0367118 A1 | 12/2015 | Scherkowski |
| 2016/0000646 A1 | 1/2016 | Scherkowski |
| 2016/0038176 A1 | 2/2016 | Smith |
| 2016/0074646 A1 | 3/2016 | Norman |
| 2016/0121093 A1 | 5/2016 | Fan |
| 2016/0263365 A1 | 9/2016 | Smith |
| 2016/0354592 A1 | 12/2016 | Juan |
| 2017/0007814 A1 | 1/2017 | Chan |
| 2017/0014609 A1 | 1/2017 | Spadoni, III |
| 2017/0065807 A1 | 3/2017 | Niven |
| 2017/0072177 A1 | 3/2017 | Oscar |
| 2017/0157382 A1 | 6/2017 | Siciliano |
| 2017/0173319 A1 | 6/2017 | McGuire |
| 2017/0354810 A1 | 12/2017 | O'Brien |
| 2018/0056054 A1 | 3/2018 | Siciliano |
| 2018/0289902 A1 | 10/2018 | Xiang |
| 2018/0360487 A1 | 12/2018 | Algeri |
| 2018/0369553 A1 | 12/2018 | Siciliano |
| 2019/0134371 A1 | 5/2019 | Johansson |
| 2019/0249289 A1 | 8/2019 | Sakio et al. |

FOREIGN PATENT DOCUMENTS

| | | | |
|---|---|---|---|
| CN | 2111680 | | 8/1992 |
| CN | 2712279 | | 7/2005 |
| CN | 201052153 | | 4/2008 |
| CN | 102469867 | | 5/2012 |
| CN | 202682550 | | 1/2013 |
| CN | 203790439 | | 8/2014 |
| CN | 204411493 | | 6/2015 |
| CN | 204502099 | * | 7/2015 |
| DE | 102016008546 | | 9/2016 |
| EP | 2944349 | | 11/2015 |
| FR | 2747927 | | 10/1997 |
| FR | 2747928 | | 10/1997 |
| GB | 2424394 | | 9/2006 |
| KR | 20090131673 | | 12/2009 |
| KR | 100973628 | | 8/2010 |
| KR | 20130116095 | | 10/2013 |
| KR | 101395100 | | 5/2014 |
| KR | 20150009459 | | 1/2015 |
| KR | 20170044510 | | 4/2017 |
| RU | 2270040 | | 2/2006 |
| RU | 2532522 | | 11/2014 |
| WO | 2010120111 | | 10/2010 |
| WO | 2011139185 | | 11/2011 |
| WO | 2014202055 | | 12/2014 |
| WO | 2015094041 | | 6/2015 |
| WO | 2015160370 | | 10/2015 |
| WO | 2016159465 | | 10/2016 |
| WO | 2016202339 | | 12/2016 |
| WO | WO 2017178069 | * | 10/2017 |
| WO | WO-2017178069 A1 | * | 10/2017 ........ A61M 37/0076 |

* cited by examiner

ELECTROMAGNETICALLY DRIVEN TATTOO MACHINE AND SYSTEM

CROSS-REFERENCE TO RELATED APPLICATIONS

This is a continuation of U.S. patent application Ser. No. 16/158,290, filed Oct. 11, 2018. The foregoing application is hereby incorporated by reference into the present application in its entirety.

BACKGROUND OF THE DISCLOSURE

The disclosure relates generally to the field of mechanical apparatuses, and more particularly, to a pen style microneedling machine apparatus actuated by magnetic means. Microneedling machines include tattoo machines, permanent makeup machines, and therapeutic skin stimulation machines. When used with hollow needles, they can be useful for implantation of temporary or permanent pigments, compounds, chemicals, large molecules and even cells beneath the skin. They can also be used with non-hollow needles to selectively injure specific layers of skin which stimulate natural healing response.

Field of the Disclosure

The present disclosure generally relates to apparatuses and systems to magnetically actuate and control a microneedle machine.

Background

Tattoo and microneedle machines generally use electric coils to drive a spring-loaded reciprocating needle structure in order to puncture the upper layers of skin and deposit small amounts of colorant into the skin. This type of machine is often bulky, heavy, and cumbersome for the operator (the tattoo artist, skin therapist, or physician), having an off-balance mass relative to the operator's hand, making it more difficult for the operator to re-orient the machine by fingertip in the operator's hand during use. These devices are also prone to overheating and produce vibration, further causing discomfort to the user and thereby shortening the length of time the device can be used over a continuous period. Environmentally for both operator and subject, they are inherently noisy during operation, thus leading to aural fatigue and shorter tattooing or therapy sessions.

Due to the nature of the prior designs, which include exposed mechanical components and electrical connections, properly cleaning, sterilizing, or autoclaving the device or its constituent components has been limited or impossible. Using non-sterilizable machines or components creates an inherent health and safety issue for the subject as well as for the operator, or leads to expensive waste in disposing of contaminated parts.

Tattoo artists, cosmetic tattooists, and microneedle therapists desire a machine that limits vibration and heat.

While electromagnetic coils have been used to actuate tattoo needles, they do so through direct mechanical connection. Traditional coil tattoo machines employ two coils fixed in a frame to produce the oscillatory rectilinear mechanical motion to a needle bar through an intermediary armature bar. These components are typically exposed to the environment, leading to potential contamination of the machine and increased noise emissions.

WO 2017/178069 describes a radial engagement utilizing two permanent magnets, but fails to eliminate all mechanical components because it employs a mechanically oscillating permanent magnet and other moving components inside the machine. Due to the oscillation of the components inside the machine, it does not eliminate vibration when the machine is in operation. It also fails to reduce the diameter of the machine, and thus fails to reduce device grip diameter.

It would, therefore, be desirable to have a machine that eliminates all moving parts within the drive unit, narrow the overall device size to improve ergonomics, can programmatically control movement of the needle through intelligently controlled circuitry, is lightweight, and vibration free.

While certain aspects of conventional technologies have been discussed to facilitate disclosure of the invention, Applicant in no way disclaims these technical aspects, and it is contemplated that the claimed invention may encompass one or more of the conventional technical aspects discussed herein.

In this specification where a document, act, or item of knowledge is referred to or discussed, that reference or discussion is not an admission that the document, act, or item of knowledge or any combination thereof was at the priority date, publicly available, known to the public, part of common general knowledge, or otherwise constitutes prior art under the applicable statutory provision; or is known to be relevant to an attempt to solve any problem with which this specification is concerned.

BRIEF SUMMARY OF THE DISCLOSURE

The following presents a simplified summary of the disclosure in order to provide a basic understanding of some aspects of the disclosure. This summary is not an extensive overview of the disclosure. It is intended neither to identify key or critical elements of the disclosure nor to delineate the scope of the disclosure. Its sole purpose is to present some concepts of the disclosure, in accordance with the disclosure, in a simplified form as a prelude to the more detailed description presented later.

In one embodiment, a contactless, motion-free microneedle drive apparatus for oscillating one or more microneedles is disclosed. The drive apparatus comprises a housing which includes a receiving end adapted to detachably couple with a needle cartridge, the receiving end thus defines a substantially cylindrical socket for receiving the needle cartridge, the receiving end is characterized by a continuous surface that forms a physical barrier between the needle cartridge and the interior of the housing, and the housing further includes a second end such that the receiving end and the second end define an axis, the drive apparatus further includes at least one electromagnet within the housing which is isolated from the needle cartridge, and the electromagnet is oriented such that it develops a magnetic field aligned substantially parallel to the axis and which magnetically interacts with and drives a ferrous component slidably constrained within the needle cartridge.

In another embodiment of the disclosure, a contactless microneedle system is provided which includes a drive apparatus and a needle cartridge. The drive apparatus includes housing with a receiving end adapted to detachably couple with a needle cartridge, the receiving end thus defines a substantially cylindrical socket for receiving the needle cartridge, the receiving end forms a continuous surface that creates a physical barrier between the needle cartridge and the interior of the housing, and the housing further includes a second end such that the receiving end and the second end define an axis, the drive apparatus further includes at least one electromagnet within the housing which is isolated from the needle cartridge, and the electromagnet is oriented such that it develops a magnetic field aligned substantially parallel to the axis. The contactless microneedling system further includes a needle cartridge that comprises a cartridge housing divided into a needle nozzle and an insertable portion. Inside the cartridge housing is a needle assembly comprising a needle slide, at least one needle, and a needle driver attached to the needle slide such that the needle assembly is allowed to reciprocate in a limited amount of displacement within the cartridge housing and the needle nozzle allows the needle to protrude from the needle cartridge while the insertable portion reversibly mates with the receiving portion of the needle driver unit. The electromagnet is oriented in the drive unit so that it develops a magnetic moment aligned substantially parallel to the axis and adapted to magnetically interact with and drive the needle assembly while the needle cartridge is constrained within the socket.

A further embodiment is method of operating a microneedle system, the method including the steps of providing an electromagnetically powered needle drive unit, providing a needle cartridge having an axis and a ferromagnetic driver, the electromagnetically powered drive unit creates an axially-oriented magnetic moment which magnetically engages the ferromagnetic driver in a contactless manner by the axially oriented magnetic moment, and manipulating the magnetic field produced by the electromagnet to reciprocate a needle within the needle cartridge along the axis.

Embodiments of the present disclosure may include components manufactured from various materials based upon the contemplated use. For embodiments that are contemplated for human use, materials that are durable, cleanable or autoclaveable, and sanitary are contemplated to be within the scope of the present invention. By way of example and not limitation, materials may be stainless steel, anodized aluminum, or polycarbonates.

The present disclosure may address one or more of the problems and deficiencies of the prior art discussed above. However, it is contemplated that the invention may prove useful in addressing other problems and deficiencies in a number of technical areas. Therefore the claimed invention should not necessarily be construed as limited to addressing any of the particular problems or deficiencies discussed herein.

The following description and the annexed drawings set forth certain illustrative aspects of the disclosure. These aspects are indicative of only some of the various ways in which the principles of the disclosure may be employed, and the present disclosure is intended to include all such aspects and their equivalents. Other advantages and novel features of the disclosure will become apparent from the following description when considered in conjunction with the drawings.

BRIEF DESCRIPTION OF THE DRAWINGS

The disclosure can be readily understood by considering the following detailed description in conjunction with the accompanying drawings, in which.

DETAILED DESCRIPTION

The following detailed description and the appended drawings describe and illustrate various embodiments of the disclosure solely for the purpose of enabling one of ordinary skill in the relevant art to make and use the disclosure. As such, the detailed description and illustration of these embodiments are purely exemplary in nature and are in no way intended to limit the scope of the disclosure, or its protection, in any manner. It should also be understood that the drawings are not to scale and in certain instances details have been omitted, which are not necessary for an understanding of the present disclosure, such as conventional details of fabrication and assembly.

In the Summary above, in the Description, and in the accompanying drawings, reference is made to particular features of the disclosure. It is to be understood that the disclosure in this specification includes all possible combinations of such particular features. For example, where a particular feature is disclosed in the context of a particular aspect or embodiment of the invention, or a particular claim, that feature can also be used, to the extent possible, in combination with and/or in the context of other particular aspects and embodiments of the disclosure, and in the disclosure generally.

The term "comprises" and grammatical equivalents thereof are used herein to mean that other components, structures, steps, etc. are optionally present. For example, an article "comprising" (or "which comprises") components A, B, and C can consist of (i.e., contain only) components A, B, and C, or van contain not only components A, B, and C, but also one or more other components or structures.

The term "at least" followed by a number is used herein to denote the start of a range beginning with that number (which may be a range having an upper limit or no upper limit, depending on the variable being defined). For example, "at least 1" means 1 more than 1. The term "at most" followed by a number is used herein to denote the end of a range ending with that number (which may be a range having 1 or 0 as its lower limit, or a range having no lower limit, depending upon the variable being defined). For example, "at most 4" means 4 or less than 4, and "at most 40%" means 40% or less than 40%. When, in this specification, a range is given as "(a first number) to (a second number)" or "(a first number)-(a second number)," this means a range whose lower limit is the first number and whose upper limit is the second number. For example, 25 to 100 mm means a range whose lower limit is 25 mm, and whose upper limit is 100 mm.

The term "mechanical features" is used herein to mean features of a component, mechanical or geometric, which have a functional purpose of attaching or linking that component to one or more other components with compatible or corresponding mechanical features. An example of a mechanical feature is a slot in a component, where said slot is designed to accept a tab from another component and the union of the slot and tab from the two components effectively links, attaches, fixes, and/or locks the components together. The term "mechanical features" refers to, but is not limited to: hooks, hook and loop fasteners, slot and tabs, all male and female fasteners, screws, bolts, nuts, holes that have been tapped, latches, pins, etc.

While the specification will conclude with claims defining the features of embodiments of the disclosure that are regarded as novel, it is believed that the disclosure will be better understood from a consideration of the following description in conjunction with the figures, in which like reference numerals are carried forward.

In one embodiment, a contactless, motion-free microneedle drive apparatus for oscillating one or more microneedles is disclosed. The drive apparatus comprises a housing which includes a receiving end adapted to detachably couple with a needle cartridge, the receiving end thus defines a substantially cylindrical socket for receiving the needle cartridge, the receiving end is characterized by a continuous surface that forms a physical barrier between the needle cartridge and the interior of the housing, and the housing further includes a second end such that the receiving end and the second end define an axis, the drive apparatus further includes at least one electromagnet within the housing which is isolated from the needle cartridge, and the electromagnet is oriented such that it develops a magnetic field aligned substantially parallel to the axis and which magnetically interacts with and drives a ferrous component slidably constrained within the needle cartridge.

In another embodiment, the contactless, motion-free microneedle drive apparatus the electromagnet may define a hollow cylinder which is positioned within the housing to at least partially encompass a portion of the socket. In another variation of the embodiment, the cylinder may be co-incident with the socket, such that the socket essentially forms an inner sleeve of the electromagnetic coil.

In a further embodiment, the electromagnet of the contactless, motion-free microneedle drive apparatus may have a ferromagnetic core. The core may extend beyond the end of the coil windings to further focus or amplify the magnetic field in the approximate area of the needle assembly.

In yet another embodiment in accordance with the disclosure, the contactless, motion-free microneedle drive apparatus might incorporate a hall effect 202 sensor placed inside the housing on the internal surface of the socket such that the sensor 202 may measure displacement of a needle assembly contained within the needle cartridge. Multiple hall effect sensors 202 may be provided parallel to the axis to more accurately monitor the precise displacement of the needle.

In still further embodiments, the contactless, motion-free microneedle drive apparatus may include one or more heat pipes 303 in thermal communication with each electromagnet and be configured to draw heat away from the electromagnet towards a heatsink area at another location on the housing such that head can be discharged into the environment outside of the housing, and away from an operator's hand.

In other embodiments, the contactless, motion-free microneedle drive apparatus may be powered by one or more batteries contained within the housing. The battery power source may be controlled by electronic circuitry designed to programmatically control delivery of power from the batteries to each of the electromagnets.

In another embodiment of the disclosure, a contactless microneedle system is provided which includes a drive apparatus and a needle cartridge. The drive apparatus includes housing with a receiving end adapted to detachably couple with a needle cartridge, the receiving end thus defines a substantially cylindrical socket for receiving the needle cartridge, the receiving end forms a continuous surface that creates a physical barrier between the needle cartridge and the interior of the housing, and the housing further includes a second end such that the receiving end and the second end define an axis, the drive apparatus further includes at least one electromagnet within the housing which is isolated from the needle cartridge, and the electromagnet is oriented such that it develops a magnetic field aligned substantially parallel to the axis. The contactless microneedling system further includes a needle cartridge that comprises a cartridge housing divided into a needle nozzle and an insertable portion. Inside the cartridge housing is a needle assembly comprising a needle slide, at least one needle, and a needle driver attached to the needle slide such that the needle assembly is allowed to reciprocate in a limited amount of displacement within the cartridge housing and the needle nozzle allows the needle to protrude from the needle cartridge while the insertable portion reversibly mates with the receiving portion of the needle driver unit. The electromagnet is oriented in the drive unit so that it develops a magnetic moment aligned substantially parallel to the axis and adapted to magnetically interact with and drive the needle assembly while the needle cartridge is constrained within the socket.

In yet another embodiment, the contactless microneedle system may include a control unit that supplies a direct current to each electromagnet. It may further include electronic circuitry to programmatically control the electrical power supplied to the electromagnet.

A further embodiment is method of operating a microneedle system, the method including the steps of providing an electromagnetically powered needle drive unit, providing a needle cartridge having an axis and a ferromagnetic driver, the electromagnetically powered drive unit creates an axially-oriented magnetic moment which magnetically engages the ferromagnetic driver in a contactless manner by the axially oriented magnetic moment, and manipulating the magnetic field produced by the electromagnet to reciprocate a needle within the needle cartridge along the axis.

The electromagnetic tattoo system according to the disclosure includes a needle within the cartridge which is in magnetic communication with an electromagnetic coil housed within the tattoo needle driving machine. The needle assembly may include a permanent magnet which has a magnetic moment aligned in a first direction essentially parallel with the reciprocation axis. When the needle cartridge is engaged in the receiving portion of the tattoo machine, the needle is driven outward from the cartridge housing by a magnetic moment developed by the electromagnet which is opposite to the moment of the permanent magnet of the needle assembly.

Additional electromagnets may be provided within the drive machine, each adapted for specific magnetic moments, or orientations of the magnetic fields developed so as to control the oscillation of the needle assembly.

In some embodiments, the electromagnet may have a ferromagnetic core to increase the strength of the magnetic field developed by the coil. In other embodiments, the coil may wind around a portion of the machine housing that is specially adapted to receive and mate with a needle cartridge. This socket area may define an approximately cylindrical hollow into which the rear portion of a needle cartridge may correspondingly mate in a fixed but reversible fashion. The coil may entirely surround the socket inside the housing, or may only partially surround the socket. The choice of the number of windings, wire thickness of the windings, and current delivered to the coil may be selectively designed to tailor the device to particular applications. For example, some microneedling applications may require significantly higher magnetic field applied to the needle so that the drive force of the needle into a target substance, such as animal hide which is tougher than human skin, allows the device to operate effectively.

From a strictly physical perspective, a magnet may consist of atoms or microscopic regions of opposing magnetic moments, which together sum to a macroscopic magnetic moment. However, throughout this disclosure, the term "magnetic moment" or "magnetic field" refers to the macroscopic phenomenon only, i.e. for an aggregate, integrated magnetic moment, corresponding to an overall magnetic polarity.

One electromagnetic coil may develop a magnetic moment which has the same polarity orientation as a permanent magnet within the needle cartridge. Consequently, as the electromagnetic coil produces a magnetic field, it repels the permanent magnet and the needle that is in physical communication with the permanent magnet is projected outward from the cartridge. Upon withdrawing the field, the tension device retracts the needle back into the housing. This repeated magnetic field development and extinguishment thus produces the oscillation required to apply tattoo ink to an individual's skin. Alternatively, a second electromagnetic coil may be provided within the driver housing. It may have the same or an opposite winding or the same or an opposite flow of current so as to develop a magnetic field having opposite polarity as the first electromagnet, or a combined stronger single magnetic field synergistically with the first.

Instead of providing a tension device within the needle cartridge, the second coil could attract the permanent magnet, thus retracting the needle into the cartridge housing. Magnetic fields may be alternatively developed and extinguished between the two electromagnets to produce rapidly changing magnetic polarity. The changing polarity of the electromagnets thus repels and attracts the permanent magnet in the needle cartridge to produce the desired linear oscillating motion of the needle. The coils may also be operated independently of each other to create varying magnetic fields.

One or more coils may surround the cartridge socket, and one or more coils may be positioned directly behind the end of the cartridge socket. The coils may be operated independently to produce varying acceleration, velocity, inertia, or momentum of the needle, which thus provides the operator with control over the needle's "give," "throw," "stroke," speed or frequency, and other desirable control parameters to optimize the intended use of the machine.

An electromagnetically controlled microneedle may be powered internally by one or more batteries. The batteries may be charged by induction rather than direct electrical connections. In this embodiment, the components contained within the housing may be completely isolated from the needle cartridge, operator's hand, and surrounding environment—thus making the whole drive unit cleanable without the need for unit disassembly. Electronic circuitry may be provided inside the drive unit to control the delivery of power to the electromagnet. Alternatively, the electronic circuitry may be in communication wirelessly with a remote control unit.

Alternatively, an electromagnetically controlled microneedle may be powered externally through conventional tattoo power supplies.

Regarding control of the drive unit, an electromagnetically actuated microneedle machine may be controlled in a more finite way than conventional systems allow through selective development and extinguishment of the magnetic field. Electronic circuitry may be provided to control one or multiple electromagnets which to vary the size, orientation, and intensity of the magnetic moment. Changes in the magnetic field affects the needle velocity and displacement or reciprocation according to the magnetic moment developed by one or several coils. In this way, one or more discrete logic-controlled magnetic fields may be created, extinguished, and altered in intensity and duration to control the needle assembly. Complex electronic signals can be sent to the electromagnet to vary the needle's oscillation, protrusion, and force of application. By way of example and not limitation, pulse width modulation may allow an operator temporal and spatial control over the needle displacement.

A needle cycle consists of a starting point and some displacement from that starting point, followed by a return to that same starting point. For example, one needle cycle may consist of a needle starting from a resting or retracted position and extending outward to a fully extended position, and subsequently returning to the same initial resting position. One or more periods may define a needle cycle, each period having a beginning time, a beginning position, an ending time, and an ending position. Alternatively, a period may be defined as having a beginning time, a beginning velocity, an ending time, and an ending velocity.

By way of further and not limitation, a needle cycle may comprise a needle moving from fully retracted position to fully extended position, then to a partially retracted position, then returning to a fully extended position, then to a partially retracted position, back to the fully extended position, and then finally return to the fully retracted position. In this example, during a single needle cycle a needle may be oscillated while the tip of the needle remains embedded in the target skin before being withdrawn from the skin. Sequences of periods may be varied to produce different needle cycles. Needle cycles may vary from one cycle to the next.

A cycle may optionally require predefined events to occur before continuing in the cycle. By way of example and not limitation, the needle may be held stationary in an extended position, allowing the operator to visually inspect the needle before requiring operator input to continue with the cycle. As a further example, a cycle may be intelligently programmed to dynamically respond to resistive force encountered by the needle during a cycle. This on the fly automatic adjustment of a cycle provides greater flexibility to an operator to achieve specific objectives of a microneedling session.

Additionally, needle periods and needle cycles may be programmed into a control unit that controls an electromagnetic coil. The control unit may also monitor different electric signals generated by the coil in response to the environment, or may be in communication with separate dedicated sensors.

A magnetic tattoo machine may optionally include one or more sensors. The device may include a hall effect sensor to determine the position of the needle assembly. Other sensors may include gyroscopes that provide information regarding the spatial orientation of the device, temperature sensors, accelerometers to provide information about the acceleration of the combined cartridge-device system or about the acceleration of the needle relative to the device, magnetometers, proximity sensors that may work in conjunction with a patient-subject, with a control unit, or with other components and supplies used by the operator.

Alternatively, an optical sensor may be provided in the receiving portion on the device. The sensor may determine the position of the needle by optically engaging with a reflective component integral with the cartridge needle assembly.

These sensors may provide information to a control unit which powers and controls the signals sent to the electromagnetic coil.

The control unit may dynamically alter the field produced by the electromagnetic coil through machine learning. By way of example and not limitation, the control unit may compare the intended acceleration of the needle during a needle cycle period to the actual measured acceleration of the needle to determine the resistance of the target skin. It may further associate that computed difference in acceleration with the orientation of the combined cartridge-device system, and develop a spatial array of a patient's skin as the tattooing or microneedling session progresses. When an operator returns to a particular locus within the array, the control unit may alter the intended acceleration of the needle to ensure optimal needle speed or penetration depth. Further benefits of machine learning functionality within the control unit may include optimizing energy efficiency, ink delivery or deposit, or therapeutic stimulation of the patient's skin.

A magnetic tattoo machine may optionally include cooling features configured to dissipate heat generated by the coil and selectively discharge it away from an operator's hand. In some embodiments, one or more heat pipes, heat spreaders, or a combination of heat pipe and heat spreaders may be configured to surround the coil and extend rearward along the axis of the machine away from the area where the operator's hand engages the machine. The evaporator portion of the heat pipe may be selectively placed near high heat-producing areas of the coil, while the condenser portion is located a distance from the evaporator, preferably in an area on the machine away from the operator's hand. The heat pipe thus removes heat produced by the coil and conducts it towards heat discharging features on the machine. Such discharging features may include fins or other designs which increase the surface area to promote heat transfer from the heat pipe into the surrounding environment. The heat dissipating features may be integral to the housing. Optionally, the grip area on the machine may be constructed of material to insulate the operator's hand from the coil and heat pipe.

In various embodiments of the disclosure, one or more needles are contained within a cartridge that correspondingly mates with an opening on the machine defining a socket to reversibly receive and hold a portion of the needle cartridge during operation of the system. Needles may be hollow or solid.

The cartridge is configured such that there is no mechanical link between the needle and drive source housed within the tattoo machine. While the cartridge itself may include various features that permit it to be reversibly engaged by the cartridge receiver portion of the machine, the needle is operated in a contactless fashion by the magnetic field developed by the coil. The rear portion of the cartridge which is inserted into the receiving portion of the machine may be completely sealed to mechanically isolate the components housed within the cartridge from the drive source.

The needle is attached to a needle slide, which is in turn attached to a permanent magnet. The needle, needle slide, and magnet comprise a needle assembly which is allowed to slidingly oscillate within the cartridge housing. The magnet is adapted to slide, via linear displacement, within the cartridge and so as to magnetically couple to a magnetic field developed by the electromagnetic coil.

The needle cartridge or nozzle may include a tension device that applies repulsive force between the cartridge or nozzle and the needle assembly. Tension devices may include a spring or an elastomeric material adapted to keep the needle assembly in a retracted position inside the cartridge whenever no magnetic field is present. The force of the tension device may vary, depending on the specific implementation of an electromagnetic drive machine. By way of example and not limitation, the spring force may be sufficient to maintain the needle assembly in a retracted position. An alternative example may require significantly higher spring force to more rapidly retract the needle assembly into the cartridge housing to provide the retraction function during operation of the system.

In some embodiments, a resilient material may be provided within the cartridge housing or as a component of the needle assembly and positioned between the needle assembly and the interior of the housing to function as a cushion to reduce the force of impact between the needle assembly and cartridge housing as it retracts into the cartridge housing from a forward position. Cushions may include elastomeric bumpers, a rubber disk or O-ring.

In some embodiments, the needle assembly may include a ferromagnetic material adapted to respond to the magnetic moment developed by the electromagnetic contained within the housing of the drive unit. In other embodiments, the needle assembly may include a permanent magnet adapted to respond to the magnetic moment developed by the electromagnetic contained within the housing of the drive unit.

The cartridge may have an internal stabilizing component which mechanically connects the magnet to the needle. In combination with an internal lip inside the cartridge housing, the stabilizing component may limit the needle's maximum overall travel. Travel of the needle may be adjusted by altering the length of the stabilizing component.

The cartridge housing may have a plurality of holes oriented on opposite sides of the central axis for flushing, rinsing, or cleaning the needle during operation. Opposite-facing openings on the forward portion of the cartridge housing allow the tip of the cartridge housing to be dipped into a cleaning or flushing solution, and moved from side to side in such a way that cleaning fluid more easily enters the cartridge, minimizes turbulent flow and reduces formation of vacuum to more effectively rinse the needle and needle assembly. The openings may further be oriented parallel to the central axis, or at an acute angle relative to the axis and inward towards the tip of the needle cartridge. These acute, forward-facing openings further aid in the reduction of splash-back of ink or rinsing solution to the operator.

Knurling or other friction-increasing features may also be provided on the cartridge housing to enhance manipulation, including to enhance finger grip removal of the cartridge from the tattoo machine.

Figure 1:
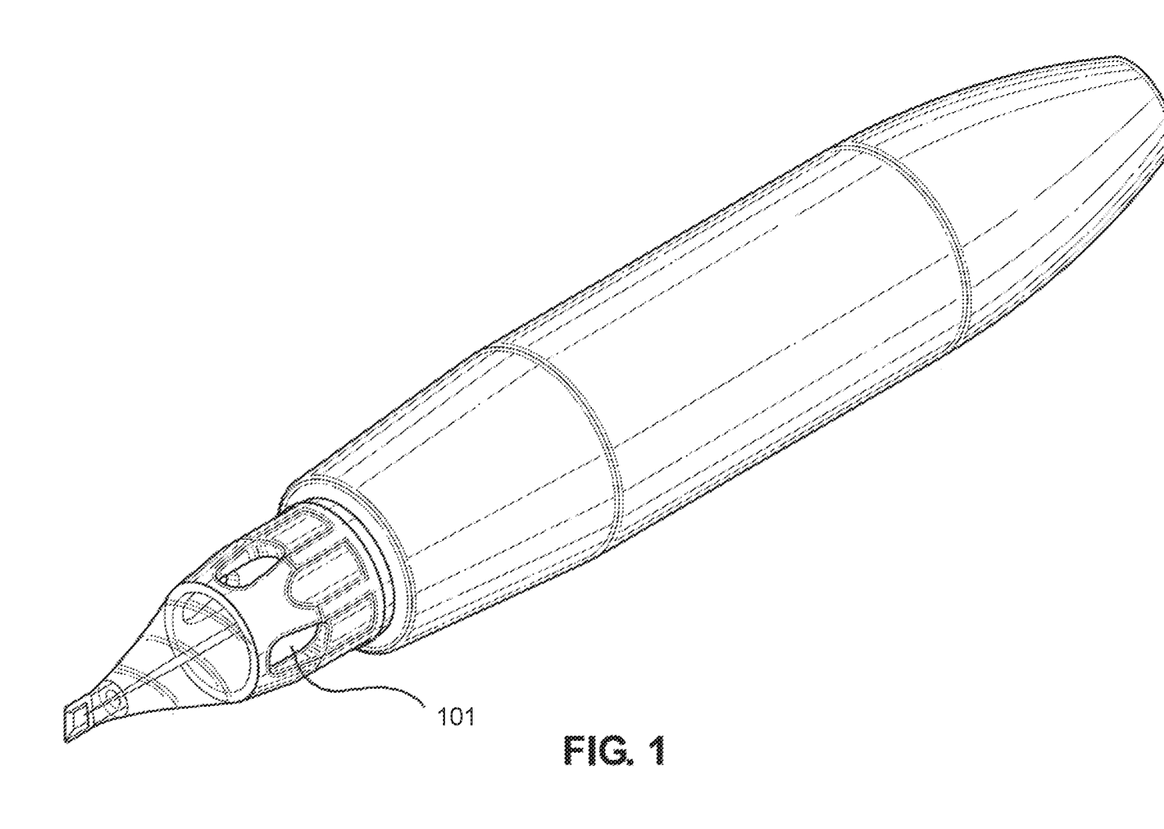
FIG. 1 illustrates a perspective view of an embodiment of a contactless microneedle system in accordance with the disclosure comprising an electromagnetically operated driver unit and needle cartridge.

Now, with reference to FIG. 1, an embodiment of a contactless, motion-free microneedle drive system is provided in accordance with the disclosure. The drive unit is shown together with a needle cartridge inserted into the receiving end. The needle cartridge includes at least two apertures 101 positioned opposite one another. When the combined driver-cartridge system is being operated, the tip of the cartridge may be dipped, or immersed in a cleansing solution to wash out ink as the operator transitions from one color to another during a tattoo session. The apertures face towards the needle nozzle end of the cartridge to direct any potential splash-back away from the grip area, and thus away from an operator's hand.

Figure 2:
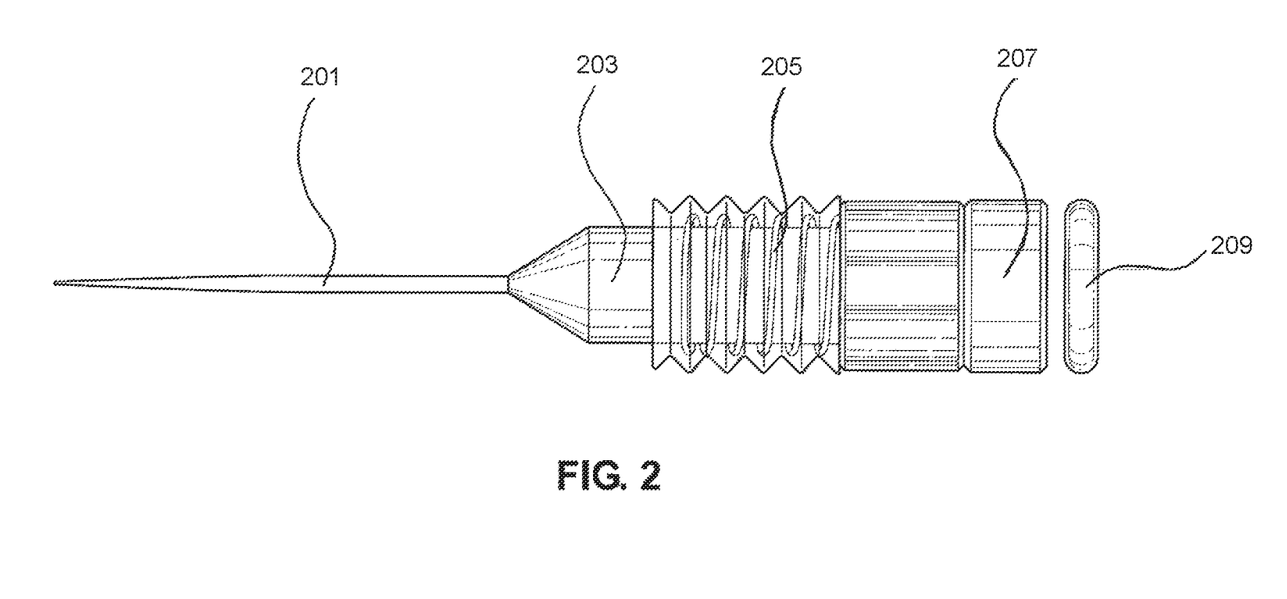
FIG. 2 illustrates a lateral view of an embodiment of a magnetically driven microneedle assembly in accordance with the disclosure comprising a needle, a needle slide, a spring, a spring boot, a permanent magnet, and a bumper.

Now, with reference to FIG. 2, an embodiment of the needle assembly is disclosed. A needle assembly contained within a needle housing may consist of a needle 201 connected to a needle slide 203. About the outer circumference of the needle slide a spring 205 is provided which applies repulsive force between the bottom end of the needle slide and an internal facet of the needle cartridge housing. Attached to the bottom of the needle slide is a permanent magnet 207. Situated between the magnet and the inner surface of the needle cartridge housing is a rubber O-ring 209. As the spring applies force between the needle slide and cartridge housing, the magnet encounters the O-ring bumper upon retraction to reduce harsh impacts and vibration when the system is operating.

Figure 3:
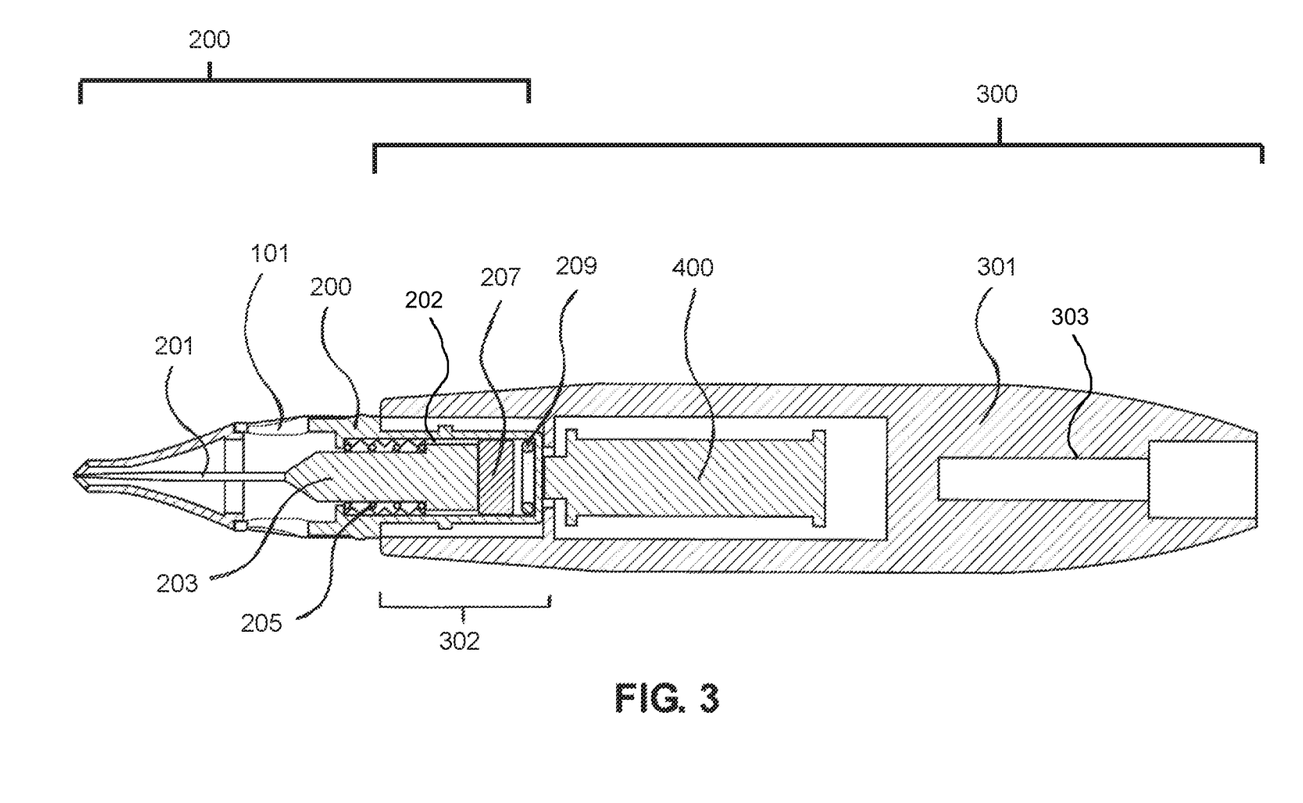
FIG. 3. Illustrates a lateral cross sectional view of an embodiment of a contactless microneedle system in accordance with the disclosure comprising a driver housing, an electromagnet, a needle cartridge socket integral with the housing, and a magnetically actuated needle cartridge inserted into the cartridge socket.

Turning to FIG. 3, an embodiment of a contactless, motion-free microneedle drive system is provided in accordance with the disclosure. The system includes a drive unit 300 and a needle cartridge 200. The drive unit 300 includes a drive unit housing 301 with a cartridge receiving portion 302 on the working end of the drive unit housing 301. Contained within the housing 301 is an electromagnet 400 oriented parallel with the longitudinal length of the drive unit 300 and parallel to the axis of reciprocation of the needle assembly. The electromagnet 400 may include one or more separate windings to fine tune the development of the magnetic field. The needle cartridge includes a housing 200 with openings 101 along the sides to permit fluid to freely enter the interior of the cartridge housing. A needle assembly is slidably constrained within the housing and includes a needle 201, a needle slide 203, a spring 205, a permanent magnet 207, and a bumper O-ring 209. The needle assembly remains in a retracted position due to the force applied by the spring 205 situated between features on the interior of the cartridge housing and a spring shoulder on the needle slide. Mating features retain the rear portion of the cartridge within the drive unit receiving portion 302.

As referenced in this disclosure and claims, "a microneedle" is not to be construed as a structural limitation, but is instead descriptive of the functional result of the disclosed structure. Needles may not be micro sized, but instead the term generically describes small needles, and the verb microneedling describes a rectilinear motion wherein the needle is rapidly inserted and withdrawn from the skin of a person or animal.

In light of the foregoing description, it should be recognized that embodiments in accordance with the present invention can be realized in numerous configurations contemplated to be within the scope and spirit of the claims. Additionally, the description above is intended by way of example only and is not intended to limit the present invention in any way, except as set forth in the claims.

In addition, though the disclosure has been described in reference to several examples optionally incorporating various features, the disclosure is not to be limited to that which is described or indicated as contemplated with respect to each variation of the disclosure. Various changes may be made to the disclosure described and equivalents (whether recited herein or not included for the sake of some brevity) may be substituted without departing from the true spirit and scope of the disclosure. In addition, where a range of values is provided, it is understood that every intervening value, between the upper and lower limit of that range and any other stated or intervening value in that stated range, is encompassed within the disclosure.

Also, it is contemplated that any optional feature of the inventive variations described may be set forth and claimed independently, or in combination with any one or more of the features described herein. Reference to a singular item, includes the possibility that there are plural of the same items present. More specifically, as used herein and in claims associated hereto, the singular forms "a," "an," "said," and "the" include plural referents unless the specifically stated otherwise. In other words, use of the articles allow for "at least one" of the subject item in the description above as well as claims associated with this disclosure. It is further noted that such claims may be drafted to exclude any optional element. As such, this statement is intended to serve as antecedent basis for use of such exclusive terminology as "solely," "only" and the like in connection with the recitation of claim elements, or use of a "negative" limitation.

Without the use of such exclusive terminology, the term "comprising" in claims associated with this disclosure shall allow for the inclusion of any additional element—irrespective of whether a given number of elements are enumerated in such claims, or the addition of a feature could be regarded as transforming the nature of an element set forth in such claims. Except as specifically defined herein, all technical and scientific terms used herein are to be given as broad a commonly understood meaning as possible while maintaining claim validity.

The breadth of the present disclosure is not to be limited to the examples provided and/or the subject specification, but rather only by the scope of claim language associated with this disclosure.

What is claimed:

1. A needle cartridge for a tattoo system, the needle cartridge comprising:
a cartridge housing that defines a working end section that defines an opening, and a drive unit end section that is substantially sealed with a continuous surface that creates a physical barrier between the needle cartridge and a drive unit of the tattoo system, the drive unit end section being detachably coupled to a working end of the drive unit of the tattoo system; and
a needle assembly comprising a magnetic element housed within the cartridge housing;
wherein the needle assembly is urged to move longitudinally in a reciprocating motion when the magnetic element of the needle assembly is subjected to a magnetic field generated by one or more electromagnets housed within the drive unit and having a magnetic moment substantially parallel to a longitudinal axis of the needle assembly,
wherein the one or more electromagnets of the drive unit and the magnetic element of the needle assembly are co-linear, physically spaced apart along the longitudinal axis without overlapping and physically disconnected such that the magnetic element of the needle assembly is capable of moving relative to the one or more electromagnets of the drive unit.

2. The needle cartridge according to claim 1, wherein the magnetic element is positioned on a drive unit end of the needle assembly, wherein a magnetic moment generated by a first electromagnet of the one or more electromagnets causes the needle assembly to move in a first direction and a magnetic moment generated by a second electromagnet of the one or more electromagnets causes the needle assembly to move in a second direction that is opposite the first direction.

3. The needle cartridge according to claim 1, further comprising a resilient member, wherein the resilient member applies a force to the needle assembly towards the drive unit end of the cartridge housing.

4. The needle cartridge according to claim 3, wherein the resilient member compresses when at least one of the one or more electromagnets of the drive unit is energized.

5. The needle cartridge according to claim 1, wherein the needle assembly comprises a slide section and the one or more needles extend from a working end of the slide section, wherein the slide section comprises a cylindrically shaped body portion having a first diameter and a head portion having a second diameter that is greater than the first diameter, wherein the cylindrically shaped body portion is positioned on a working end side of the slide section, and the head portion is positioned on a drive unit end side of the slide section.

6. The needle cartridge according to claim 5, wherein the magnetic element is positioned on the head portion of the slide section of the needle assembly.

7. The needle cartridge according to claim 5, further comprising a helical spring configured to urge the needle assembly in a direction towards the drive unit end of the cartridge housing to retract the one or more tips of the one or more needles within the cartridge housing, wherein the cylindrically shaped body portion of the slide section of the needle assembly extends through a central passage of the helical spring.

8. The needle cartridge according to claim 7, wherein the cartridge housing comprises an inner ledge that extends from an inner surface of the cartridge housing, wherein the helical spring is held in place between the inner ledge of the cartridge housing and the head portion of the slide section.

9. The needle cartridge according to claim 1, further comprising a bumper positioned at the drive unit end of the cartridge housing, wherein the bumper absorbs an impact of the needle assembly against the drive unit end of the cartridge housing that would otherwise occur when at least of the one or more electromagnets of the drive unit is de-energized.

10. The needle cartridge according to claim 1, wherein the drive unit end section of the cartridge housing is configured to be releasably secured within an opening of a working end of the drive unit.

11. The needle cartridge according to claim 1, wherein the working end section of the cartridge housing defines a tattoo ink entry opening.

12. A tattoo system comprising:
a drive unit; and
a needle cartridge, wherein the needle cartridge comprises:
  a cartridge housing that defines a working end section that defines an opening, and a drive unit end section that is substantially sealed with a continuous surface that creates a physical barrier between the needle cartridge and the drive unit of the tattoo system, the drive unit end section being detachably coupled to a working end of the drive unit of the tattoo system; and
  a needle assembly comprising a magnetic element housed within the cartridge housing;
  wherein the needle assembly is urged to move longitudinally in a reciprocating motion when the magnetic element of the needle assembly is subjected to a magnetic field generated by one or more electromagnets housed within the drive unit and having a magnetic moment substantially parallel to a longitudinal axis of the needle assembly;
  wherein the one or more electromagnets of the drive unit and the magnetic element of the needle assembly are co-linear, physically spaced apart along the longitudinal axis without overlapping and physically disconnected such that the magnetic element of the needle assembly is capable of moving relative the one or more electromagnets of the drive unit.

13. The tattoo system according to claim 12, wherein the magnetic element is positioned on a drive unit end of the needle assembly, wherein a magnetic moment generated by a first electromagnet of the one or more electromagnets causes the needle assembly to move in a first direction and a magnetic moment generated by a second electromagnet of the one or more electromagnets causes the needle assembly to move in a second direction that is opposite the first direction.

14. The tattoo system according to claim 12, further comprising a resilient member, wherein the resilient member applies a force to the needle assembly towards the drive unit end of the cartridge housing.

15. The tattoo system according to claim 14, wherein the resilient member compresses when at least one of the one or more electromagnets of the drive unit is energized.

16. The tattoo system according to claim 12, wherein the needle assembly comprises a slide section and the one or more needles extend from a working end of the slide section, wherein the slide section comprises a cylindrically shaped body portion having a first diameter and a head portion having a second diameter that is greater than the first diameter, wherein the cylindrically shaped body portion is positioned on a working end side of the slide section, and the head portion is positioned on a drive unit end side of the slide section.

17. The tattoo system according to claim 16, wherein the magnetic element is positioned on the head portion of the slide section of the needle assembly.

18. The tattoo system according to claim 17, further comprising a helical spring configured to urge the needle assembly in a direction towards the drive unit end of the cartridge housing to retract the one or more tips of the one or more needles within the cartridge housing, wherein the cylindrically shaped body portion of the slide section of the needle assembly extends through a central passage of the helical spring.

19. The tattoo system according to claim 18, wherein the cartridge housing comprises an inner ledge that extends from an inner surface of the cartridge housing, wherein the helical spring is held in place between the inner ledge of the cartridge housing and the head portion of the slide section.

* * * * *